US008573062B2

(12) United States Patent
Zhao et al.

(10) Patent No.: US 8,573,062 B2
(45) Date of Patent: Nov. 5, 2013

(54) IMPLANTABLE MICRO-ELECTROMECHANICAL SYSTEM SENSOR

(75) Inventors: Yong D. Zhao, Simi Valley, CA (US); Apratim Dixit, Burbank, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/365,005

(22) Filed: Feb. 2, 2012

(65) Prior Publication Data

US 2012/0130219 A1    May 24, 2012

Related U.S. Application Data

(62) Division of application No. 11/750,575, filed on May 18, 2007, now Pat. No. 8,127,618.

(51) Int. Cl.
*G01L 7/00* (2006.01)
*A61N 1/365* (2006.01)
*A61B 5/0215* (2006.01)
*A61B 5/00* (2006.01)
*G01L 9/00* (2006.01)

(52) U.S. Cl.
CPC ............... *A61B 5/0215* (2013.01); *A61B 5/686* (2013.01); *A61B 5/6869* (2013.01); *G01L 9/0073* (2013.01)
USPC ............................... 73/754; 607/119; 607/23

(58) Field of Classification Search
USPC ..................................... 73/700–754
See application file for complete search history.

(56) References Cited

U.S. PATENT DOCUMENTS

| 4,967,755 | A | 11/1990 | Pohndorf |
| 5,353,800 | A | 10/1994 | Pohndorf et al. |
| 5,466,254 | A | 11/1995 | Helland |
| 7,017,419 | B2 | 3/2006 | Pedersen et al. |
| 7,024,936 | B2 | 4/2006 | Pedersen et al. |
| 7,114,397 | B2 | 10/2006 | Fortin et al. |
| 7,762,138 | B2 | 7/2010 | Zdeblick et al. |
| 7,935,056 | B2 | 5/2011 | Zdeblick et al. |
| 2004/0057589 | A1 | 3/2004 | Pedersen et al. |
| 2005/0096706 | A1 | 5/2005 | Salo |
| 2005/0103112 | A1 | 5/2005 | Pedersen et al. |
| 2005/0288596 | A1 | 12/2005 | Eigler et al. |
| 2005/0288604 | A1 | 12/2005 | Eigler et al. |
| 2005/0288722 | A1 | 12/2005 | Eigler et al. |

(Continued)

FOREIGN PATENT DOCUMENTS

WO    2006062275 A1    6/2006

OTHER PUBLICATIONS

Restriction Requirement, mailed Aug. 29, 2011—U.S. Appl. No. 11/750,575.

(Continued)

*Primary Examiner* — Andre Allen

(57) ABSTRACT

The disclosure relates in some aspects to an implantable pressure sensor and a method of measuring pressure. In some embodiments pressure may be measured through the use of an implantable lead incorporating one or more pressure sensors. In some aspects a pressure sensor is implemented in a micro-electromechanical system ("MEMS") that employs direct mechanical sensing. A biocompatible material is attached to one or more portions of the MEMS sensor to facilitate implant in a body of a patient. The MEMS sensor may thus be incorporated into an implantable lead for measuring blood pressure in, for example, one or more chambers of the patient's heart.

6 Claims, 14 Drawing Sheets

(56) References Cited

U.S. PATENT DOCUMENTS

| | | |
|---|---|---|
| 2006/0063354 A1 | 3/2006 | Fortin et al. |
| 2009/0171413 A1 | 7/2009 | Zenati et al. |
| 2010/0016918 A1* | 1/2010 | Mann et al. .................. 607/23 |
| 2010/0042175 A1 | 2/2010 | Liu et al. |
| 2010/0082087 A1* | 4/2010 | Silipo et al. ................ 607/126 |
| 2010/0204766 A1 | 8/2010 | Zdeblick et al. |
| 2013/0102858 A1* | 4/2013 | Hill et al. .................. 600/301 |

OTHER PUBLICATIONS

Notice of Allowance, mailed Nov. 14, 2011—U.S. Appl. No. 11/750,575.

* cited by examiner

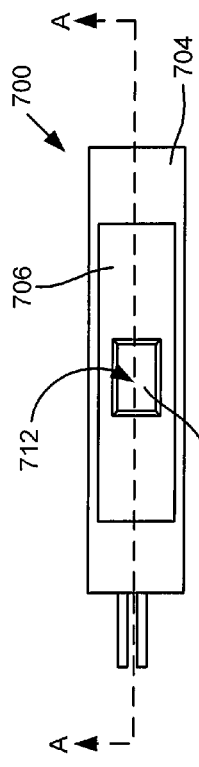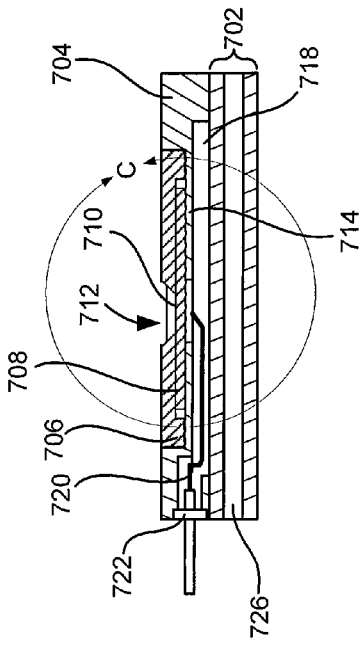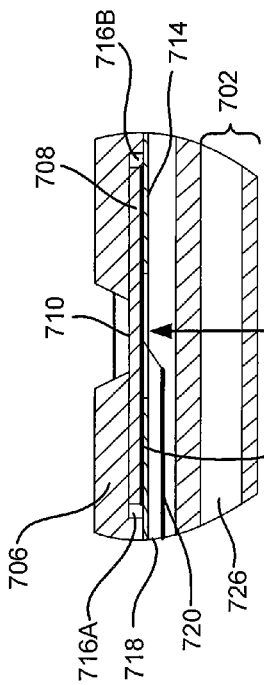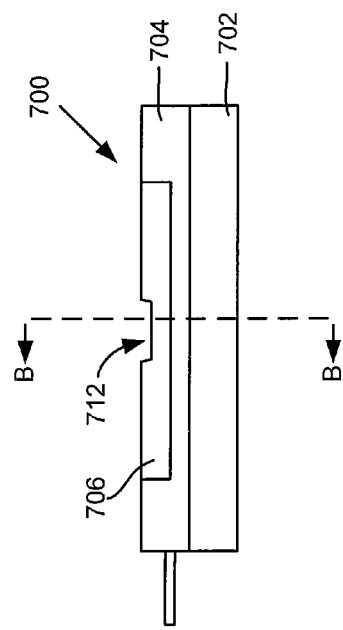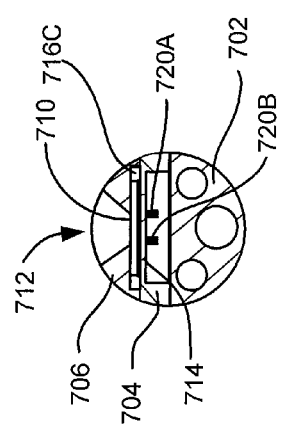
FIG. 7A
FIG. 7B
FIG. 7C
FIG. 7D
FIG. 7E

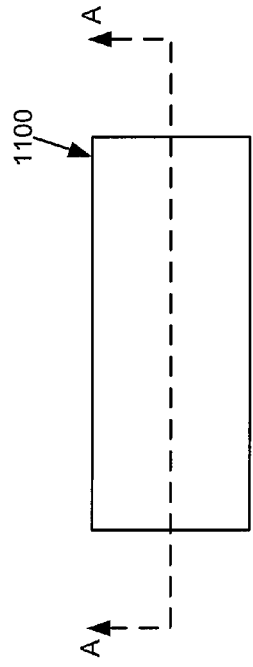
FIG. 11A
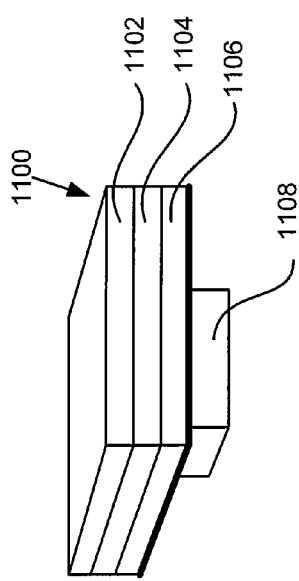
FIG. 11B
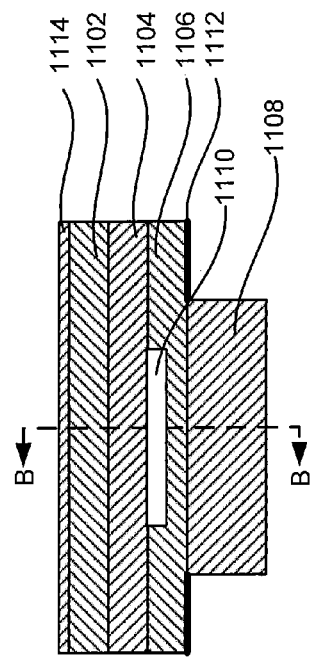
FIG. 11C
FIG. 11D
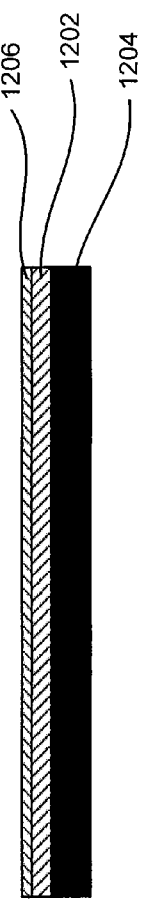
FIG. 12

IMPLANTABLE MICRO-ELECTROMECHANICAL SYSTEM SENSOR

CROSS REFERENCE TO RELATED APPLICATION

This application is a division of copending U.S. patent application Ser. No. 11/750,575, filed May 18, 2007, titled "Implantable Micro-Electromechanical System Sensor."

TECHNICAL FIELD

This application relates generally to medical devices, and to a micro-electromechanical system ("MEMS") pressure sensor for an implantable lead.

BACKGROUND

When a person's heart does not function normally due to, for example, a genetic or acquired condition, various treatments may be prescribed to correct or compensate for the condition. For example, pharmaceutical therapy may be prescribed for a patient or an implantable cardiac device may be implanted in the patient to improve the function of the patient's heart.

In conjunction with such therapy it may be desirable to detect conditions in or apply therapy to one or more chambers of the heart. Accordingly, a typical implantable cardiac device may perform one or more functions including sensing signals generated in the heart, pacing the heart to maintain regular contractions and providing defibrillation shocks to the heart.

To facilitate these sensing and therapy operations, an implanted cardiac device may attach to one or more implantable leads that extend from the cardiac device to one or more implant sites located within, on or near the heart. For example, a cardiac device may be implanted in the chest of the patient beneath the subcutaneous fat of the chest wall and above the muscles and bones of the chest. A set of leads may then be routed from the device through a vein and into the patient's heart. Alternatively, the leads from a cardiac device implanted as discussed above or at some other location may be routed to the heart via the pericardial space. In either case, distal portions of the leads are placed at locations within, on, or adjacent the heart such that electrodes on the leads are positioned at desired locations for sensing, pacing, defibrillation or other operations.

In some applications it may be desirable to measure pressure in one or more chambers of the heart or at some other location in a patient's body. For example, cardiac blood pressure readings may be used to detect various cardiac conditions such as congestive heart failure. By measuring cardiac blood pressure, conditions such as these may be detected and in some cases the patient's therapy may be modified to compensate for these conditions. As an example, if cardiac blood pressure is measured over time, the operation of an implanted cardiac device such as a cardioverter defibrillator may be adjusted or medication may be administered, as necessary, based on the conditions diagnosed as a result of the pressure measurements.

To measure cardiac pressure or other pressure in a patient, a pressure sensor may be incorporated into an implantable lead. For example, in some applications a lead may include a pressure sensor along with other components such as electrodes that may be used to sense electrical signals or apply electrical stimulation therapy. In other applications a pressure sensor may be incorporated into a dedicated lead.

Some types of pressure sensors utilize direct mechanical sensing. In a sensor employing a direct mechanical sensing mechanism, a diaphragm or other component of the sensor that is used to measure pressure is in direct mechanical contact with the medium to be sensed. For example, such a sensor may include a diaphragm on an external wall whereby the sensor measures the pressure directly applied to the diaphragm by the medium.

A direct mechanical sensing sensor may be implemented in various ways. For example, a strain gauge-based sensor may include a flexible membrane (a diaphragm) upon which one or more semiconductor stain gauges are mounted. Here, a change in pressure causes deflection of the membrane which, in turn, results in a change in the resistance of the strain gauge which may then be correlated to the change in pressure. Alternatively, a capacitor-based sensor may include a capacitor structure that includes a flexible metal membrane separated via a gap from a free-loading standoff plate. Here, a change in pressure causes deflection of the membrane which, in turn, results in a change in the capacitance of the capacitor which may then be correlated to the change in pressure.

Other types of pressure sensors employ indirect mechanical sensing. For example, a sensor module may incorporate a sensor within a sensor housing where a diaphragm of the sensor is in contact with a fluid, a gel, or some other material that facilitates the transfer of pressure waves. An outer wall of the sensor housing includes a diaphragm that also is in contact with the pressure transfer material. In this case, a change in pressure imparted on the outer diaphragm causes pressure waves to be transferred through the pressure transfer material to the diaphragm of the sensor.

In practice, sensors such as those discussed above may be relatively large (e.g., having a diameter greater than 9 French) due to physical constraints relating to the construction of the sensor. Such constraints may relate to, for example, size limitations of the strain gauge or the capacitor, sensor mounting technologies, or flexible membranes. As a result, it may be undesirable to incorporate such sensors into implantable cardiac leads having relatively small diameters (e.g., on the order of 4-6 French) because the large sensors may make it more difficult to route the lead through small spaces or around sharp corners.

Moreover, these types of sensors may not provide sufficient accuracy to measure certain pressure-related conditions in a patient. For example, a sensor employing direct mechanical sensing may not generate output signals that are correlated in a sufficiently linear manner with changes in pressure. In addition, such a sensor may have unacceptable levels of drift. The above problems may be caused by various factors relating to the design and construction of a sensor including, for example, the thickness of a metal diaphragm (e.g., on the order of 0.001 inches), the interface between a sensor housing and the flexible membrane, distortion caused by manufacturing processes such as welding or brazing, and the long term stability of adhesives or other materials used in the sensor. In addition, due to the design parameters of such a sensor, the sensor may be manufactured using a non-automated process that potentially results in a relatively low manufacturing yield.

Similarly, a sensor employing indirect mechanical pressure sensing may not provide sufficient accuracy to measure certain pressure-related conditions in a patient. For example, in general it is desirable to provide a fluid pressure inside the sensor that is identical to or has a linear relationship with the pressure external to the sensor. In practice, however, the thermal expansion and contraction properties of the pressure coupling material (e.g., fluid or gel) may be significantly different than the corresponding properties of the solid diaphragm and the inner volume holding the pressure coupling material (e.g., contraction or expansion of the space defined by the interior of the sensor housing). Consequently, changes in temperature may result in relatively large changes in the measured pressure. Moreover, the sensor may not linearly track changes in pressure when the sensor is subjected to changes in temperature. In some applications it may not be easy or practical to compensate for these deficiencies.

In view of the above, conventional sensors may not provide sufficiently accurate pressure readings or may not be of a desirable size for implant. Consequently, a need exist for an improved implantable sensor.

SUMMARY

A summary of sample aspects of the disclosure or sample embodiments of an apparatus constructed or a method practiced according to the teaching herein follows. For convenience, one or more of such aspects or embodiments may be referred to herein simply as "some aspects" or "some embodiments."

The disclosure relates in some aspects to an implantable pressure sensor and a method of measuring pressure. In some embodiments pressure may be measured through the use of an implantable lead incorporating one or more pressure sensors. Depending on the requirements of a given application, the components and methods described herein may be used for acute pressure measurements, chronic pressure measurements, or both.

The disclosure relates in some aspects to a pressure sensor implemented in a micro-electromechanical system ("MEMS"), hereafter referred to as a MEMS sensor. In some embodiments a MEMS sensor includes electrical and mechanical components and may be fabricated using a batch process or other suitable process. For example, a MEMS sensor may include a thin flexible diaphragm along with a piezoelectric component, a resistive component, a capacitive component, an inductive component, or some combination of these or other suitable components for measuring pressure.

The disclosure also relates in some aspects to a MEMS sensor that employs direct mechanical sensing. In some embodiments a biocompatible material is attached to the MEMS sensor to facilitate implant of the MEMS sensor into the body of a patient. For example, a biocompatible material may be attached to any portion of the MEMS sensor that is not biocompatible and bio-stable but that may, upon implant, be placed in direct contact with bodily fluid or internal bodily tissue. Through the use of such a biocompatible material, the MEMS sensor may be safely implanted in the patient and positioned such that is in direct contact with any medium from which pressure is to be measured.

In some embodiments a MEMS sensor is used to measure blood pressure of a patient. For example, the MEMS sensor may by incorporated into a lead that is implanted within a chamber or vasculature of a patient's heart. In this case, the MEMS sensor may be positioned such that the diaphragm of the MEMS sensor is in direct mechanical contact with the blood within the chamber or vasculature where the blood pressure is to be measured.

A sensor assembly including a MEMS sensor may incorporate various features to facilitate reliability and long term stability. In some embodiments a sensor assembly includes a rigid housing structure adapted to support a MEMS sensor and hold the MEMS sensor in place. For example, the housing may define an internal space (e.g., a cavity) of an appropriate size and shape that reduces any undesirable movement of the MEMS sensor without imparting undue stress on the MEMS sensor. In some embodiments the MEMS sensor is sized and contained within the internal space such that during thermal expansion the MEMS sensor is free to expand in at least one direction. For example, the MEMS sensor may not be rigidly fixed to the housing or it may only be fixed in one or more locations. In addition, in some embodiments a reinforcing material (e.g. a reinforcement member) is attached to a surface of the MEMS sensor. For example, in some embodiments the reinforcing material may be attached to at least a portion of a bottom surface of the MEMS sensor. The reinforcing material may facilitate supporting the MEMS sensor via a portion of the housing without attaching the MEMS sensor to the housing.

In some embodiments a MEMS sensor assembly may incorporate a support material for supporting the MEMS sensor. The support material may comprise a pliable (and in some embodiments elastic) material that is adapted to isolate or damp out thermal and mechanical loading between the MEMS sensor and the housing.

A sensor assembly may incorporate various features to facilitate incorporation of a MEMS sensor into a lead such as a cardiac sensing and/or stimulation lead. For example, a sensor assembly may incorporate one or more feed-through portions to facilitation passage of conductors or other components of an implantable cardiac lead. In addition, through the use of MEMS technology for the sensor, the sensor assembly may be sized such that may easily be incorporated into an implantable lead having a relatively small diameter.

A MEMS sensor may incorporate various features to facilitate calibration of the MEMS sensor or to otherwise adjust the readings generated by the MEMS sensor. For example, a MEMS sensor may incorporate a primary pressure sensor in combination with a reference pressure sensor and/or a temperature sensor. The MEMS sensor also may employ a compensation circuit that uses the output of the reference pressure sensor and/or the temperature sensor to adjust the output of the primary pressure sensor.

BRIEF DESCRIPTION OF THE DRAWINGS

These and other features, aspects and advantages that may relate to the invention will be more fully understood when considered with respect to the following detailed description, appended claims and accompanying drawings, wherein:

FIG. 1, including

FIG. 6, including

FIG. 7, including FIGS. 7A, 7B, 7C, 7D, and 7E, illustrates various simplified views of an embodiment of a sensor assembly;

FIG. 9, including

FIG. 11, including FIGS. 11A, 11B, 11C, and 11D, illustrates various simplified views of an embodiment of a MEMS sensor;

FIG. 12 is a simplified diagram of an embodiment relating to the use of multiple layers for applying a biocompatible material to a MEMS sensor;

FIG. 15, including

Figure 1B:
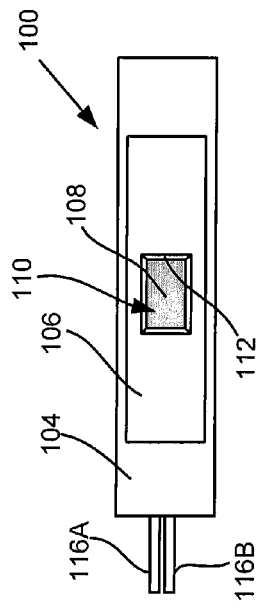
FIGS. 1A, 1B, 1C, 1D, and 1E, illustrates various simplified views of an embodiment of a sensor assembly.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The invention is described below, with reference to detailed illustrative embodiments. It will be apparent that the invention may be embodied in a wide variety of forms, some of which may appear to be quite different from those of the disclosed embodiments. Consequently, the specific structural and functional details disclosed herein are merely representative and do not limit the scope of the invention. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

In general, a micro-electromechanical system ("MEMS") is a batch-fabricated (e.g., micro-fabricated) system that contains both electrical and mechanical components with characteristic sizes ranging on the order of nanometers to millimeters. MEMS technology may be advantageously employed in sensor applications due to the potential for enhancements in performance and reliability as compared to conventional sensor technologies. Moreover, the use of MEMS technology may facilitate high integration and ease of expansion for adding new features.

In a typical application, a MEMS device is developed on a substrate (e.g., a silicon substrate). The MEMS device may thus comprise a semiconductor die constructed in several layers including various combinations of silicon, metal, and other materials. In the case of a MEMS pressure sensor, one of the layers may comprise a diaphragm that moves under pressure. In some embodiments the diaphragm layer may consist of a thin metal layer whereby slights movements of the metal diaphragm affect associated circuits. These circuits may comprise, for example, a piezo-electric circuit, a resistive circuit, a capacitive circuit, an inductive circuit, some other suitable circuit, or some combination of these circuits.

In general, silicon-based MEMS devices, by themselves, are not particular suitable for implant. For example, silicon is not sufficiently biocompatible or bio-stable for implant applications. In addition, MEMS devices tend to be relatively fragile (e.g., brittle). Various techniques are described herein for providing a MEMS sensor that may be effectively implanted.

FIG. 1 illustrates several views of an embodiment of a sensor assembly 100. The sensor assembly 100 includes a MEMS sensor and various components that serve to protect the MEMS sensor during implant. The views described below are designated with respect to the orientation of the sensor shown in FIG. 1

Figure 1D:
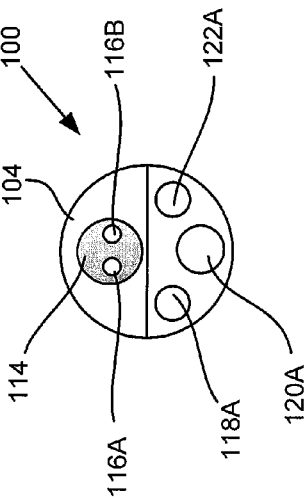
Figure 1E:
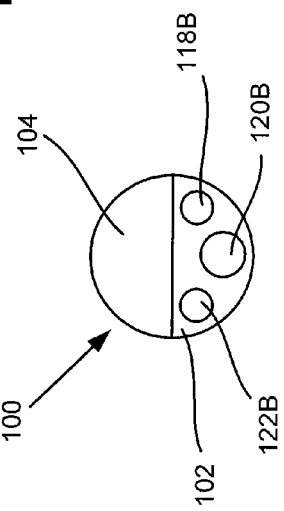
Figure 1A:
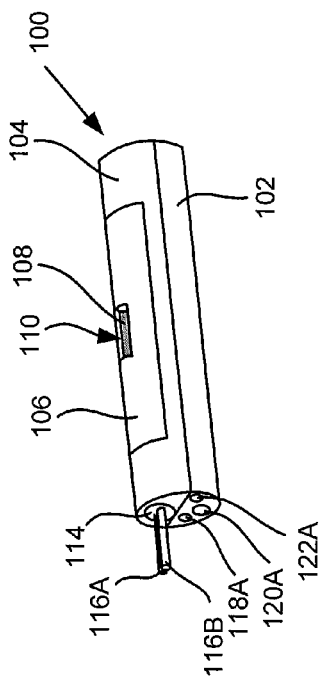

FIG. 1A illustrates a perspective view of the sensor assembly 100. The sensor assembly 100 includes a housing that comprises a feed-through portion (e.g., a bottom portion) 102 and a main sensor portion (e.g., including a top portion 104 and a cover 106 for the top portion 104). The housing encloses a MEMS sensor, a portion 108 of which is exposed through an opening (e.g., aperture) 110 in an outer wall of the housing as defined in this example by the cover 106. In general, the portion 108 comprises a diaphragm for the MEMS sensor. In some embodiments the diaphragm of the MEMS sensor may be exposed to the entire area defined by the opening 110.

Figure 1C:
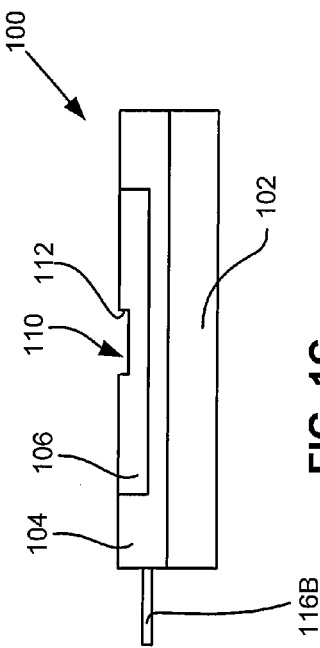

FIGS. 1B and 1C further illustrate the opening 110 that allows an external medium (e.g., blood) to directly pressure the diaphragm on the MEMS sensor. In the plan view of FIG. 1B, it may be seen that the opening 110 is defined by side portions (e.g., sidewalls) 112 in the cover 106. The front view of FIG. 1C illustrates how the opening 110 may form a recess in the curved outer surface of the cover 106. FIG. 1C also more clearly illustrates one of the sidewalls 112 defining the opening 110. The opening 110 may take various forms. For example, the opening 110 may be a non-tapered window or a tapered window (e.g., with an angle anywhere from 90 to 10 degrees with respect to a horizontal axis in FIG. 1C). In addition, the opening 110 may have a rectangular, square, elliptic, circular, or some other shape. As will be discussed in more detail below, in some aspects a layer of biocompatible material may be attached to the exposed portion of the MEMS sensor (and in some cases to at least a portion of the sidewalls) to facilitate implant of the sensor assembly 100.

Referring again to FIG. 1A, one side of the top portion 104 includes a feed-through 114 for a pair of conductors 116A and 116B. The feed-through 114 and the conductors 116A and 116B are further illustrated in the left side view of FIG. 1D.

The bottom portion 102 includes one or more feed-throughs (e.g., passageways, not shown in FIG. 1) that enable conductors or other components to pass through the sensor assembly 100. As illustrated in FIG. 1A and FIG. 1D, the left side of the bottom portion 102 includes several openings 118A, 120A, and 122A to the passageway(s). As illustrated in FIG. 1E, the right side of the bottom portion 102 includes corresponding openings 118B, 120B and 122B to the passageway(s).

In an embodiment wherein the sensor assembly 100 is incorporated into a cardiac lead, these passageways may carry pacing, sensing, defibrillation, and sensor bus conductors in the form of coils or cables. For example, a passageway associated with openings 118A and 118B may comprise a lumen carrying a pacing and/or sensing cable. In addition, a passageway associated with openings 120A and 120B may comprise a lumen carrying a shocking and/or pacing cable, while a passageway associated with openings 122A and 122B may comprise a lumen carrying a sensing cable.

Figure 2:
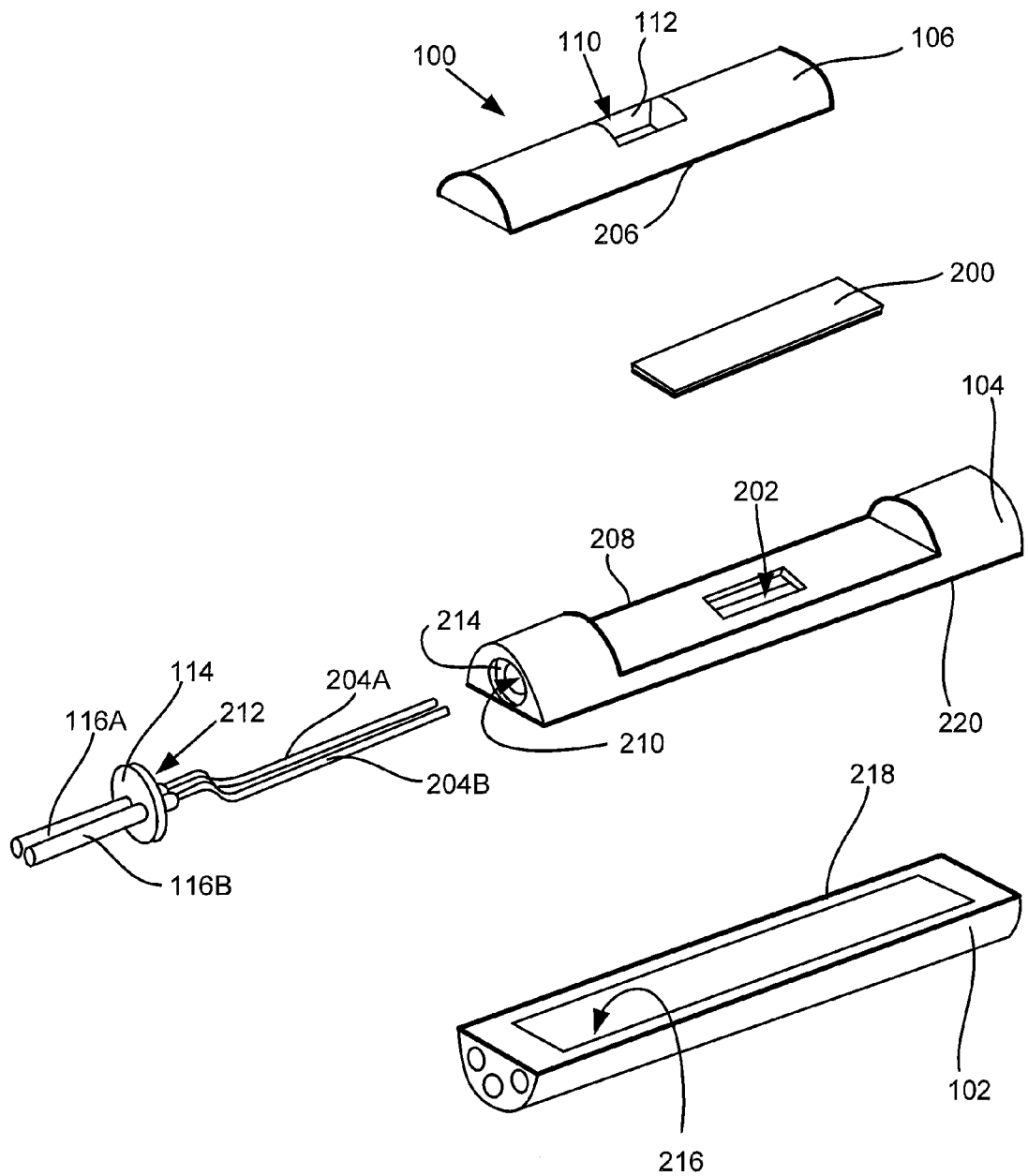
FIG. 2 is a simplified exploded diagram of an embodiment of a sensor assembly.

FIG. 2 illustrates an exploded view of an embodiment of the sensor assembly 100. In this embodiment the sensor assembly 100 includes a relatively flat MEMS sensor 200 that is housed in an inner space defined by the top portion 104 and the cover 106.

FIG. 2 also illustrates that the top portion 104 includes an opening 202 in a bottom surface through which conductors may pass. For example, conductors 204A and 204B associated with the conductors 116A and 116B, respectively, may pass through a passageway in the top portion 104 and through the opening 202 to couple to electrode pads on a bottom surface of the MEMS sensor 200. In this way, signals may be coupled between the MEMS sensor and a device (not shown in FIG. 2) coupled to the conductors 116A and 116B.

In a typical embodiment the MEMS sensor 200 is hermetically sealed within the assembled top portion 104 and cover 106 (e.g., the main sensor portion). For example, the top portion 104 and the cover 106 may be constructed of an appropriate material for hermetic sealing (e.g., metal) and these components may be joined by welding or some other technique that ensures a hermetic seal. In FIG. 2 sample weld lines on the top portion 104 and the cover 106 are represented by the thick lines 206 and 208, respectively. As will be discussed in more detail below, various techniques may be employed to ensure that the top of the MEMS sensor 200 is adequately sealed against a bottom portion of the cover 106 (e.g., in the vicinity of the opening 110). In addition, the bottom of the top portion 104 may be sealed in various ways. For example, this bottom surface may be continuous with the sides of the top portion 104 thereby enclosing the passageway of the top portion 104. Alternatively, in the event this bottom surface is open, the bottom of the top portion 104 may be sealed when it is attached to a bottom portion 102 (e.g., as discussed below) that has a continuous top surface. In some embodiments a vacuum may be created within the housing during manufacture to achieve hermetic sealing.

The feed-through 114 also may be adapted for hermetic sealing. For example, the feed-through 114 may be constructed of a suitable material such as ceramic and formed with the conductors 116A and 116B in a manner that provides a hermetic seal between the conductors 116A and 116B and the feed-through 114. In addition, the feed-through 114 may be adapted to enable a side opening 210 for the feed-through to be hermetically sealed. For example, the right side 212 of the feed-through 114 may include a metal layer or may be metalized in some other manner such that the metal on the feed-through 114 may be fused with (e.g., brazed or welded to) a metal surface 214 surrounding the opening 210.

The bottom portion 102 of the sensor assembly 100 may be coupled to the top portion 104 by various means. For example, these components may be joined by welding or some other technique. In FIG. 2 sample weld lines on the bottom portion 102 and the top portion 104 are represented by the thick lines 218 and 220, respectively. In some embodiments these components are joined in a manner that provides a hermetic seal. As shown in the example of FIG. 2, the top of the bottom portion 102 may be open to facilitate routing of conductors through passageway(s) 216 of the bottom portion or to reduce the amount of material in the bottom portion. The passageway(s) 216 may then be sealed once the bottom portion 102 is coupled to a top portion 104 having a continuous bottom surface.

Figure 3:
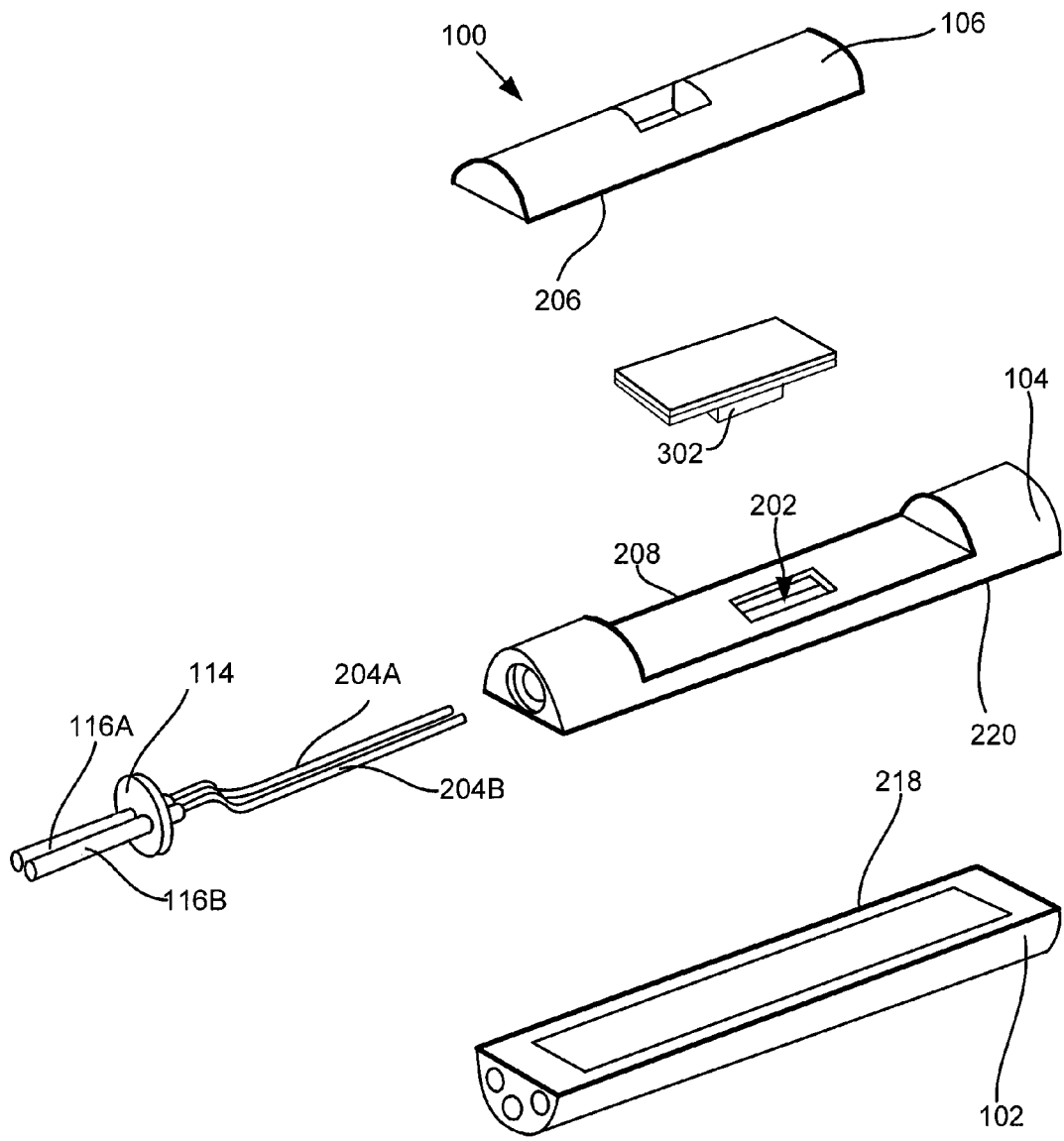
FIG. 3 is a simplified exploded diagram of an embodiment of a sensor assembly.

FIG. 3 illustrates an exploded view of another embodiment of the sensor assembly 100. The sensor assembly 100 includes a MEMS sensor 300 that is housed in an inner space defined by the top portion 104 and the cover 106. In this embodiment the MEMS sensor 300 has a smaller footprint and is implemented in more of a layered manner than the MEMS sensor 200 of FIG. 2. Consequently, the top portion 104 and the cover 106 in FIG. 3 define an inner space with different dimensions than the top portion 104 and the cover 106 in FIG. 2. In addition, the MEMS sensor 300 may include a bottom member 302 that passes at least partially into the opening 202. In this case, the conductors 204A and 204B may couple to the bottom member 302 in the passageway of the top portion 104.

The housing for the sensor assembly 100 may be constructed in various ways using a variety of materials. In some embodiments the housing components may be constructed of a biocompatible material such as titanium, titanium alloy, ceramic, MP35N, tantalum, or some other suitable material. The use of a biocompatible housing, in conjunction with the layer of biocompatible material discussed above, enables the MEMS sensor to be effectively implanted for acute or chronic applications. The housing components may be coupled together using welding, adhesives, or some other suitable technique. It should be appreciated that other suitable materials and coupling techniques may be employed depending on the needs of a particular application. In addition, various shapes and sizes may be employed for the components of the MEMS sensor assembly 100 (e.g., the housing) depending on the particular application.

The housing also may be implemented using any number of components. The housing may be constructed of several sub-components when the use of such sub-components proves to be advantageous. For example, the use of sub-components 102, 104, and 106 as shown in FIGS. 1-3 may facilitate ease of assembly and may simplify the hermetic sealing process. In other applications, however, it may prove advantageous to utilize a more unitary structure (e.g., with end caps). Moreover, in an application that does not require a passageway though the entire sensor assembly, a bottom portion (e.g., portion 102) described above may be omitted or may simply be incorporated into another sub-component.

Figure 4:
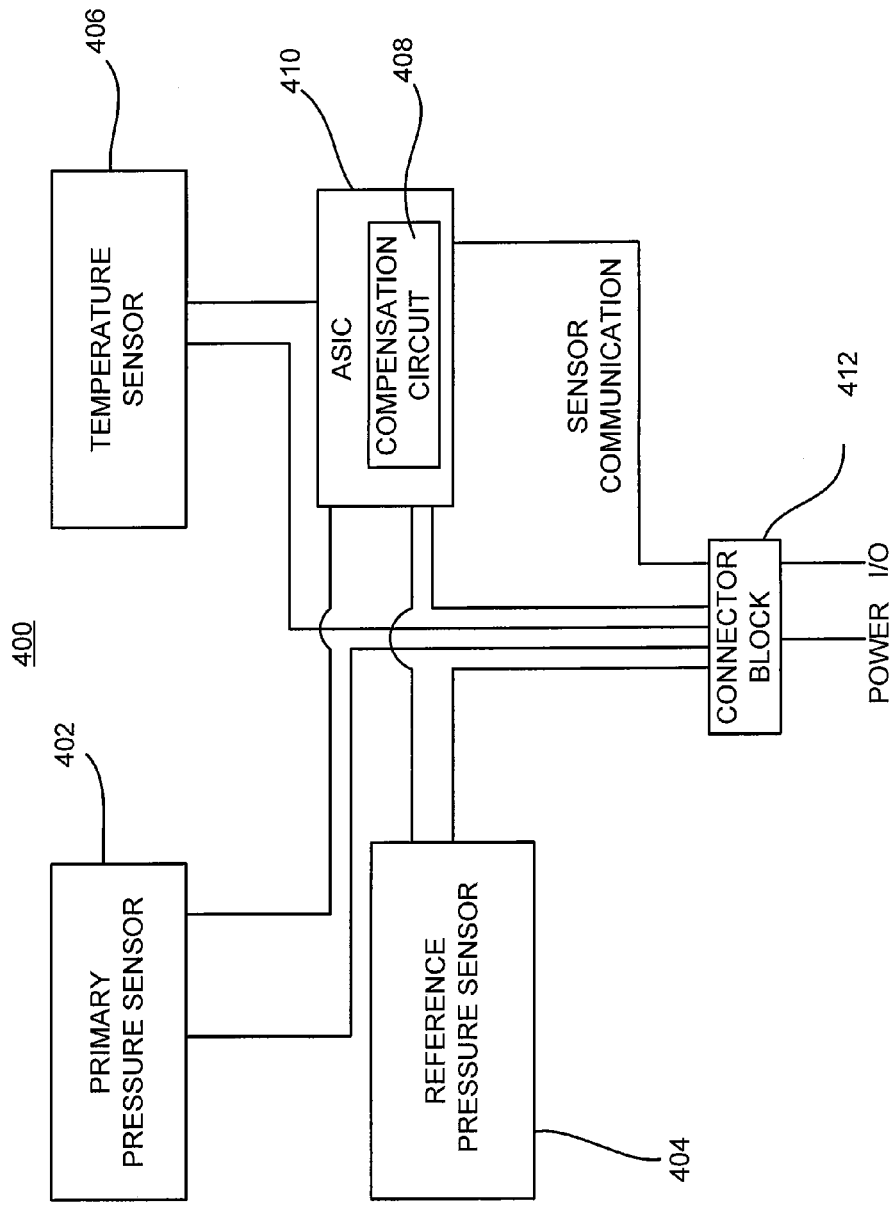
FIG. 4 is a simplified block diagram of an embodiment of a pressure sensor system.

FIG. 4 depicts a functional block diagram of an embodiment of a MEMS sensor 400. In this example, the MEMS sensor 400 includes a primary pressure sensor 402, a reference pressure sensor 404, a temperature sensor 404, and a compensation circuit 408 implemented in an application specific integrated circuit ("ASIC") 410. Each of the sensor components 402, 404, and 406 are coupled via links to the ASIC 410 to provide sensed signals to the ASIC 410. The ASIC 410, in turn, is coupled via a link to a connector block 412 thereby enabling the ASIC to communicate with one or more external devices (e.g., via one or more I/O links). In addition, all of the components are coupled to the connector block 412 to obtain power from an external device. To this end, the connector block 412 is adapted to be coupled to one or more conductors (e.g., includes electrode pads) such as conductors 204A and 204B in FIG. 2.

Sample operations relating to the generation of pressure readings will be discussed in conjunction with the flowchart of FIG. 5. For convenience, the operations of FIG. 5 (and any other operations herein) may be described as being performed by specific components. It should be appreciated, however, that these operations may be performed in conjunction with or by other components.

Figure 5:
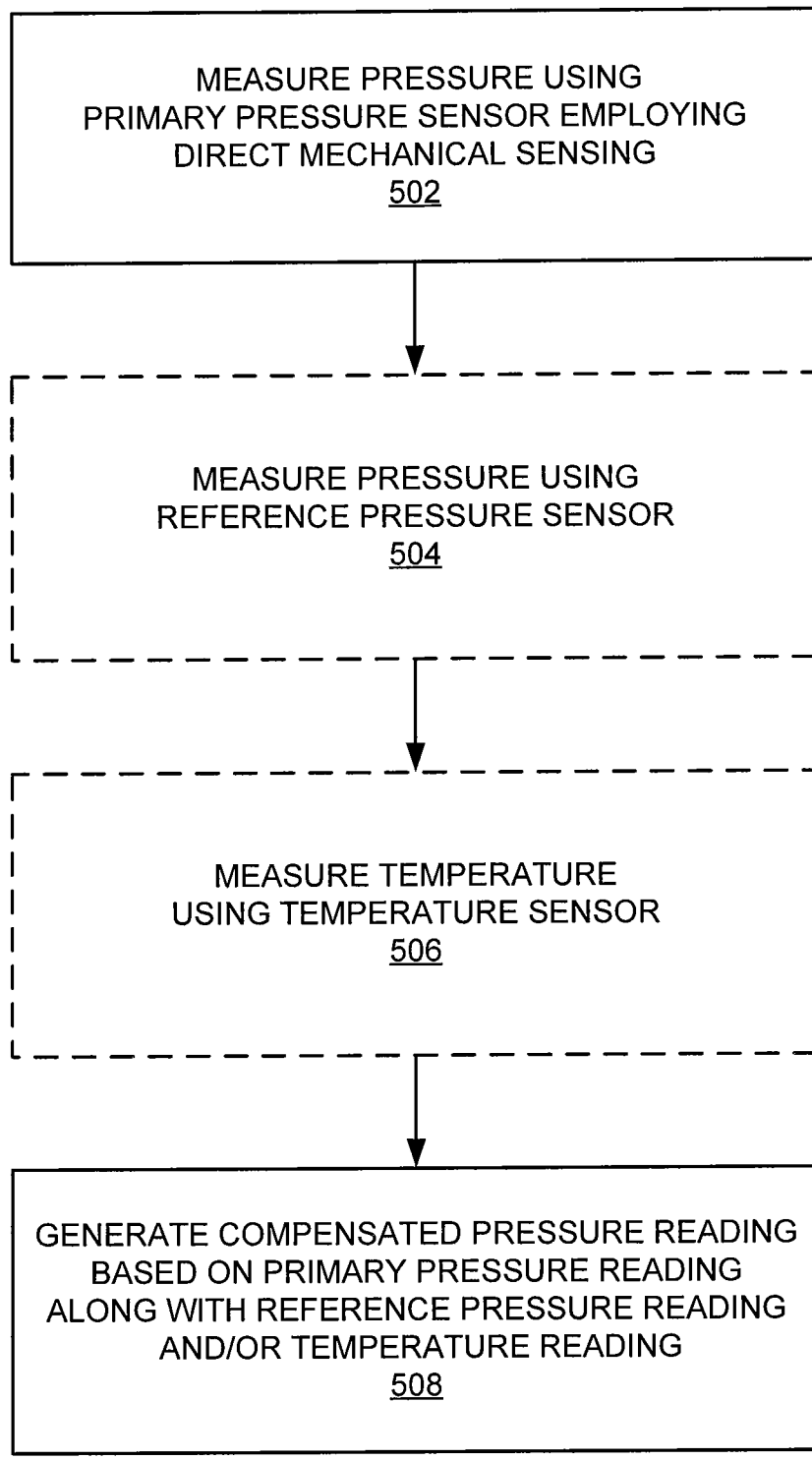
FIG. 5 is a flow chart of an embodiment of operations that may be performed to generate pressure readings.

As represented by block 502 in FIG. 5, the primary pressure sensor 402 measures pressure external to the MEMS sensor 400 to obtain a pressure reading. Thus, the MEMS sensor 400 may be constructed so that the diaphragm (not shown) of the primary pressure sensor 402 is exposed to an opening (e.g., opening 110) of the MEMS sensor 400. The primary pressure sensor 402 then generates primary pressure signals that are indicative of the measured pressure.

As represented by block 504, the reference pressure sensor 404 may optionally be used to obtain reference pressure readings. In some embodiments the diaphragm (not shown) of the reference sensor 404 is exposed to a sealed inner chamber in the MEMS sensor 400. Here, a known pressure may be maintained in the chamber for a relatively long period of time by hermetically sealing the MEMS sensor 400. Since the diaphragm of the reference pressure sensor 404 is only subjected to the sealed chamber, the reference pressure sensor 404 generates reference pressure signals that are indicative of the corresponding constant pressure. The pressure values indicated by these signals may change, however, when the MEMS sensor 400 (and, hence, the components of the MEMS sensor 400) are subjected to changes in temperature. Consequently, the reference pressure readings may be used to indicate any error in the pressure readings that result from a change in temperature of the MEMS sensor 400. As will be discussed in more detail below, this error information may be used to correct the pressure readings from the primary pressure sensor 402.

As represented by block 506, the temperature sensor 406 may optionally be used to obtain temperature readings for the MEMS sensor 400. The temperature sensor 406 generates temperature signals that are indicative of the measured temperature. This information also may be used to correct the pressure readings from the primary pressure sensor 402.

As represented by block 508, the temperature compensation operations may be performed by the compensation circuit 408. That is, the compensation circuit 408 may process the primary pressure signals, along with the reference pressure signals and/or the temperature signals, to generate a compensated pressure reading. Temperature compensation operations will be discussed in more detail with reference to FIG. 6.

Figure 6A:
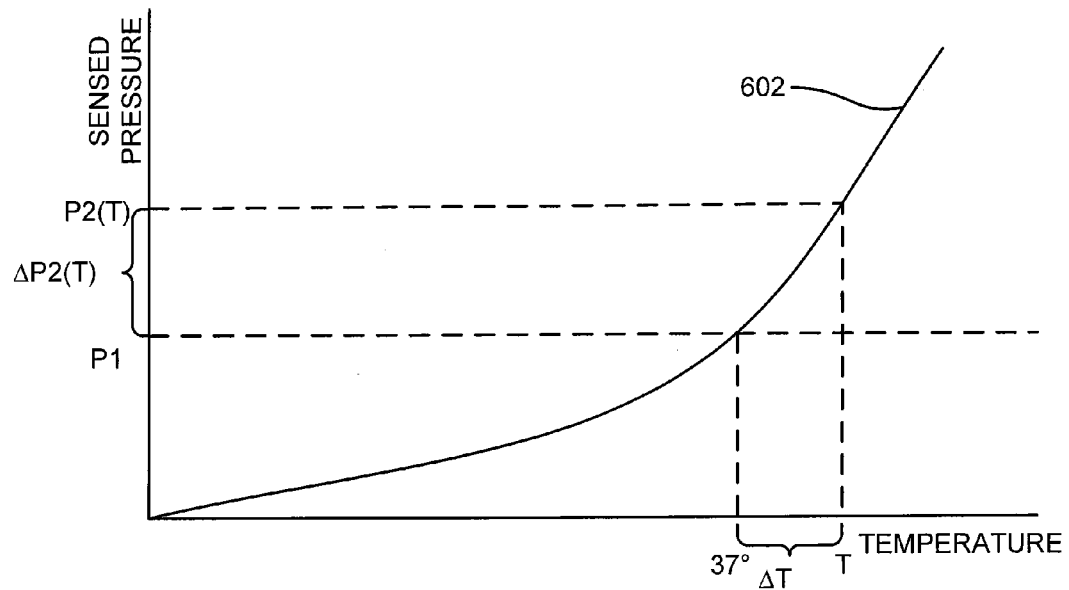
FIGS. 6A and 6B, depicts simplified graphs relating to temperature compensation.

FIG. 6A illustrates a sample plot 602 of change in sensed pressure versus change in temperature at a constant external pressure P1. At a temperature T, P1 is the actual pressure while P2 is the temperature measured by the sensor. The value ΔP2(T) is the differential pressure between P1 and P2 at temperature T.

The variation of the pressure reading (e.g., ΔP2) with various values of environmental temperature (e.g., T) may be calculated during a sensor calibration procedure and stored in a data memory. Then, during sensor operation, the output of the primary pressure sensor 402 may be combined with the appropriate value from the data memory based on the current temperature reading to cancel the temperature effect and thereby provide a temperature compensated pressure reading. Equation 1 illustrates an example compensation calculation.

$$P1(T)=P2(T)-\Delta P2(T) \qquad \text{EQUATION 1}$$

where ΔT=T−37° C.

Figure 6B:
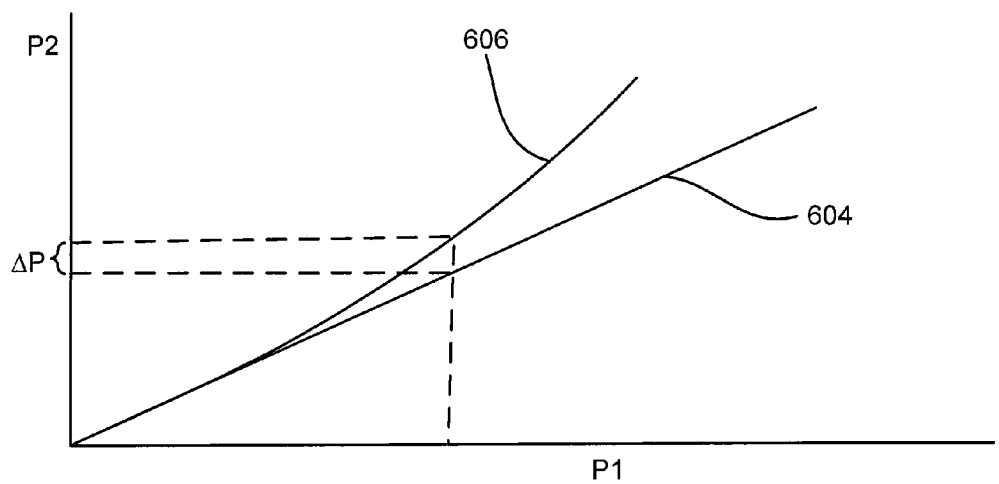

FIG. 6B depicts sample plots of P2 (sensed pressure) versus P1 (actual pressure) at a given temperature. The plot 604 represents an ideal relationship at 37° C. where P2 is equal to P1. In such a case the sensed pressure does not need to be compensated. The plot 606 represents a more typical relationship as represented by Equation 1 where P2 deviates from P1 as represented by ΔP. In such a case, temperature compensation may be provided based on signals from the temperature sensor 406 as discussed herein or in some other suitable manner.

Temperature compensation also may be provided in a similar fashion based on the reference pressure signals. For example, by providing a reference pressure sensor 404 that is substantially identical to the primary pressure sensor 402 (e.g., in terms of structure, material, fabrication, sensing mechanism, size, shape, etc.) on the same semiconductor die, both sensor 402 and 404 may have substantially similar pressure measurement characteristics, including similar temperature characteristics. In other words, the sensors 402 and 404 may generate the same pressure reading for a given temperature and pressure load. In operation, the two pressure sensors 402 and 404 will be subjected to substantially the same temperature effect since the sensors 402 and 404 are on the same die. Thus, the reference pressure sensor 404 may sense the same or substantially the same expansion loading as the primary pressure sensor 402. However, because the reference pressure sensor 404 is exposed to a substantially constant pressure, the reference pressure readings may simply reflect the change in pressure readings provided by the sensor in response to changes in temperature. A plot of this characteristic may take a form that is similar to plot 602. Thus, during sensor operation, the reference pressure signal may be combined with (e.g., subtracted from) the primary pressure signal to provide a temperature compensated pressure reading. In addition, in some applications it may prove useful to also utilize the signals from the temperature sensor 406 to provide redundant compensation (e.g., cancellation of the pressure error) for the pressure readings from the primary sensor 402.

The compensation circuit 408 may be implemented in the ASIC 410 or some other suitable processing component. The ASIC 410 also may provide other functionality for the MEMS sensor 400 including, for example, sensor calibration operations, the data memory discussed above, communication-related processing (e.g., to communicate with a device connected to the MEMS sensor 400), and other input/output ("I/O") functionality.

With the above in mind, additional details of a MEMS sensor assembly will be treated in conjunction with FIGS. 7-15. The discussion that follows relates, in particular, to various aspects that may be employed to facilitate sensor implant and reliable pressure sensor operation.

FIG. 7 illustrates several views of a sensor assembly 700. FIGS. 7A and 7B depict top and front views, respectively. FIG. 7C is a cross-section of the sensor assembly 700 from the perspective of view A-A of FIG. 7A. FIG. 7D is a cross-section of the sensor assembly 700 from the perspective of view B-B of FIG. 7B. FIG. 7E is a cross-section of the sensor assembly 700 from the perspective of view C of FIG. 7C.

The sensor assembly 700 includes a housing having a bottom portion 702, a top portion 704, and a cover 706 for the top portion 704, similar to the sensor assembly 100 discussed above. The housing encloses a MEMS sensor 708, a portion of the top surface 710 of which is exposed through an opening 712 in the cover 706. In the example of FIG. 7, the MEMS sensor 708 comprises a relatively flat structure, similar to the MEMS sensor 200 depicted in FIG. 2.

The housing components may be sized and shaped to prevent undue tension, bending, and torsion loads on the MEMS sensor 708. Preferably, the MEMS sensor 708 is subjected only to external pressure loading, and is free of any other loading. To this end, the MEMS sensor 708 may be installed in an appropriately shaped space (e.g., a groove) within the housing. For example, a MEMS sensor may be held in place without appreciable motion due to boundary constraints provided by the housing.

FIG. 7C illustrates that the MEMS sensor 708 is positioned in an inner space defined by inner surfaces of the cover 706 and a bottom wall 714 of the top portion 704. This aspect of the sensor assembly 700 is better illustrated in FIGS. 7D and 7E, and in FIG. 8 which provides a more detailed version of the view of FIG. 7D. These figures show that the inner space may be defined slightly larger than the MEMS sensor 708. For example, spaces 716A, 716B, 716C, and 716D may be provided between the sides of the MEMS sensor 708 and inner side walls of the cover 706. In addition, as is more clearly depicted in FIG. 8, a space 802A may be provided between the top of the MEMS sensor 708 and an inner bottom wall of the cover 706. Similarly, a space 802B may be provided between the bottom of the MEMS sensor 708 and an inner surface of the bottom wall 714 of the top portion 704.

Through the use of the spaces 716A-D and/or the spaces 802A-B, the housing may be adapted to secure the MEMS sensor 708 in a manner that accommodates expansion and contraction of the MEMS sensor 708 that result from changes in temperature. For example, the spaces may be sized such that when the MEMS sensor 708 has expanded due to an increase in temperature, the MEMS sensor 708 is not subjected to undue stress as a result of being constrained between the inner walls of the portion 704 and/or the cover 706. Moreover, the spaces may be sized such that when the MEMS sensor 708 has contracted, the MEMS sensor 708 is still held in place in a relatively secure manner.

In some embodiments a support material is provided in at least a portion of one or more of the spaces 716A-D and 802A-B to isolate or damp out forces or deformation due to thermal expansion, thermal contraction, vibration, and other mechanical loading that would otherwise be imparted on the MEMS sensor 708 (e.g., from the housing). For example, the support material may provide a cushioning effect to accommodate any differences between the thermal expansion characteristics of the MEMS sensor 708 and the housing. The support material may thus comprise a material that is pliable and, in some embodiments, elastic.

In some aspects the support material is adapted to be more deformable when the support material is subjected to temperatures that are above a temperature range at which pressure readings are to be made, as compared to when the support material is subjected to temperatures that are within the temperature range at which pressure readings are to be made. In this way, the MEMS sensor may be held firmly in place when pressure readings are being made because the support material will not deform to an appreciable degree when the temperature is within the specified temperature range. In contrast, when the sensor assembly 700 is subjected to higher temperatures, the support material will more readily deform, thereby allowing the MEMS sensor 708 to expand without unduly increasing stress on the MEMS sensor 708.

In some embodiments the support material may bind to the MEMS sensor 708 to hold the MEMS sensor 708 in place in the housing while allowing for thermal expansion and contraction. For example, the support material may comprise a medical adhesive, an epoxy, or some other suitable material. Such a binding material also may have pliability (e.g., deformation) properties similar to those described above.

FIG. 7 also illustrates that the sensor assembly 700 includes several passageways (e.g., inner spaces or chambers) for conductors or other components. In FIG. 7C the top portion 704 defines a passageway 718 for one or more conductors 720 (e.g., conductors 720A and 720B) that are coupled to the MEMS sensor 708 and a feed-through 722. These components may be similar to the passageway, conductors, and feed-through discussed above. FIG. 7E illustrates that the bottom wall 714 of the top portion 704 includes an opening 724 that provides access between the passageway 718 and the bottom of the MEMS sensor 708.

Figure 8:
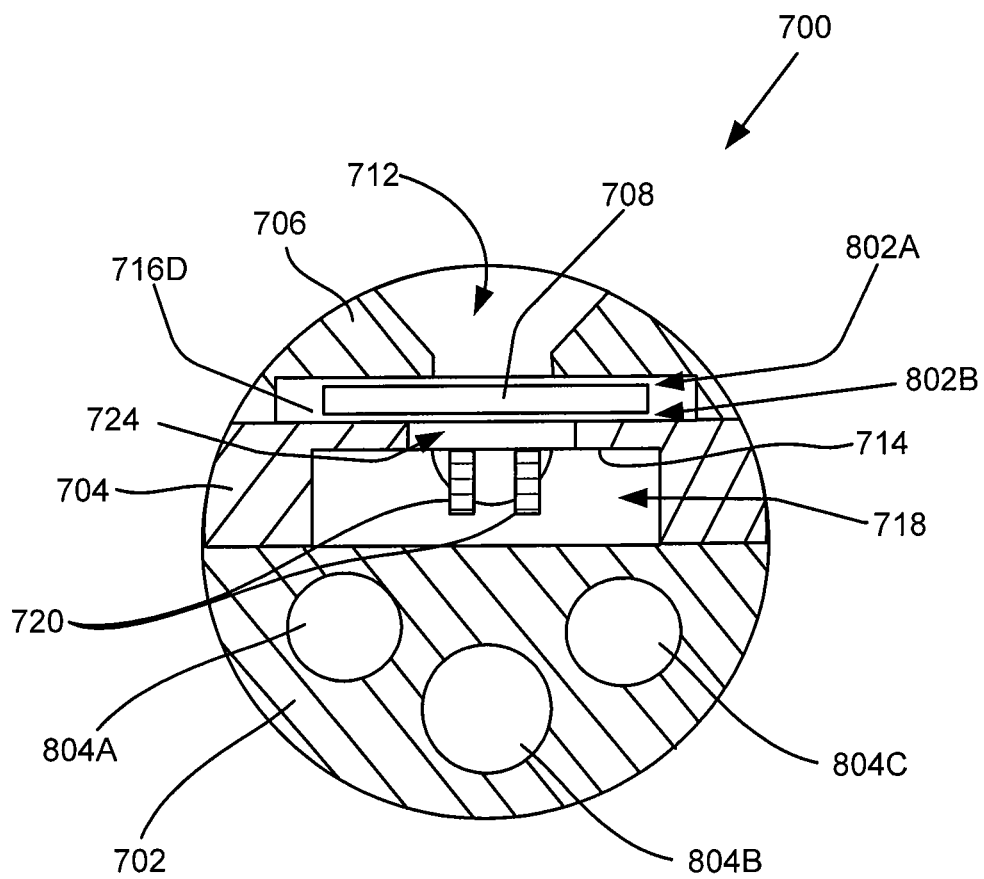
FIG. 8 is a simplified cross-sectional view of an embodiment of a sensor assembly.

The bottom portion 702 also defines a passageway 726 for one or more conductors or other components (not shown). In some embodiments the passageway 726 may comprise several passageways. For example, each of the passageways may define a lumen adapted to enable one or more conductors or other components to pass through the sensor assembly 700. As illustrated in FIG. 8, these lumens may be associated with openings 804A, 804B, and 804C in the sides of the sensor assembly 700.

Figure 9A:
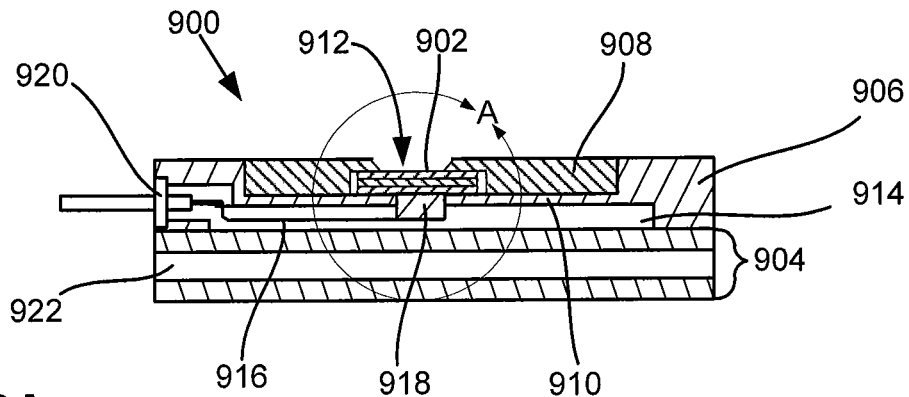
FIGS. 9A, 9B, and 9C, illustrates various simplified cross-sectional views of an embodiment of a sensor assembly.
Figure 9B:
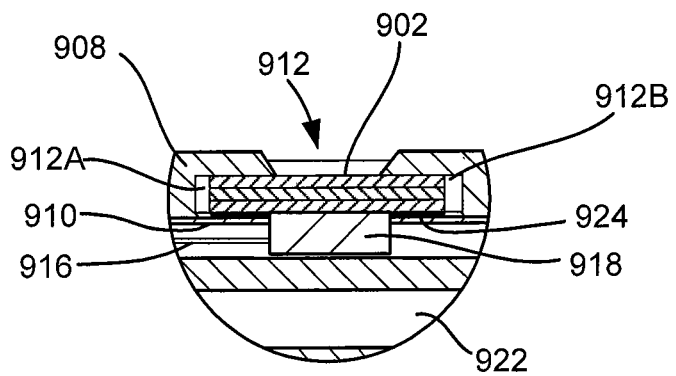
Figure 9C:
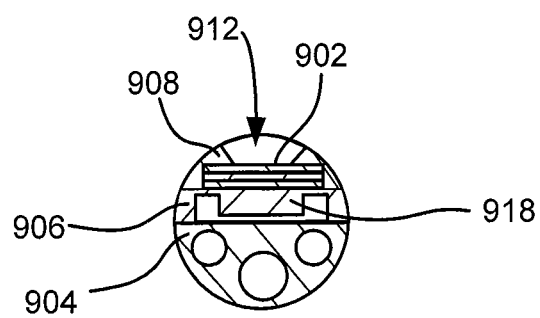
Figure 10:
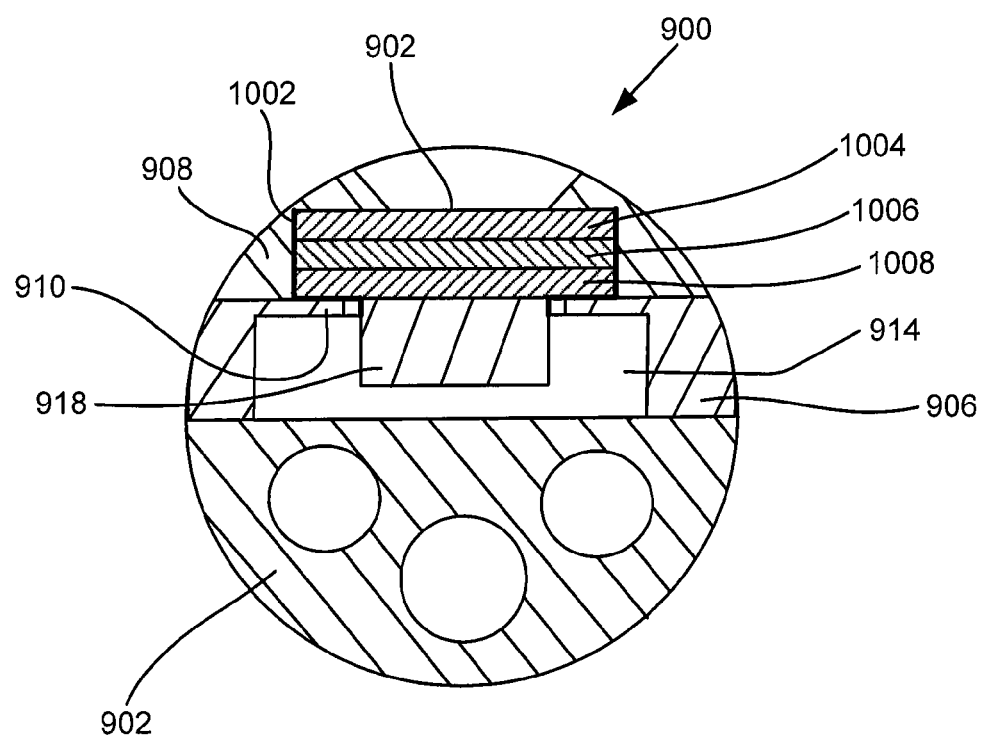
FIG. 10 is a simplified cross-sectional view of an embodiment of a sensor assembly.

FIGS. 9 and 10 illustrates several aspects of a sensor assembly 900 that includes a MEMS sensor 902 that has a smaller footprint and is implemented in a more layered manner than the MEMS sensor 708 of FIGS. 7 and 8. Thus, the MEMS sensor 902 may be similar in structure to the MEMS sensor 300 of FIG. 3. In some aspects the sensor assembly 900 may be similar in construction to the sensor assembly 700. For example, the cross-sectional views of FIG. 9A, FIG. 9B, FIG. 9C, and FIG. 10 are taken from a similar perspective as the views of FIG. 7C, FIG. 7E, FIG. 7D, and FIG. 8, respectively. In the embodiment of FIGS. 9 and 10, however, the inner space that encloses the MEMS sensor 902 has a different size and different dimensions than the inner space defined in FIGS. 7 and 8. The components of the sensor assembly 900 will be discussed briefly.

The sensor assembly 900 incorporates a housing having a bottom portion 904, a top portion 906, and a cover 908 for the top portion 906. Inner surfaces of the cover 908 and a bottom wall 910 of the top portion 906 define an inner space that encloses the MEMS sensor 902. A portion of the top surface of the MEMS sensor 902 (e.g., the diaphragm) is exposed through an opening 912 in the cover 908.

Various spaces (e.g., spaces 912A and 912B in FIG. 9B) may be provided between the sides of the MEMS sensor 902 and inner side walls of the cover 908. In addition, space may be provided between the top and bottom of the MEMS sensor 902 and, respectively, an inner bottom wall of the cover 908 and an inner surface of the bottom wall 910.

FIG. 10 illustrates an embodiment where spaces on the sides and bottom of the MEMS sensor 908 are filled with a support material 1002. In this particular example, a space is not provided above the MEMS sensor 908.

Referencing again to FIG. 9, FIG. 9B illustrates an embodiment where a reinforcing material 924 is attached to a bottom surface of the MEMS sensor 902. A similar reinforcing material 728 is shown in FIG. 7E for the MEMS sensor 708. As will be discussed in more detail below, in some embodiments the reinforcing material may adjoin an inner surface of a bottom wall (e.g., wall 910), yet not be rigidly attached to that inner surface.

The sensor assembly 900 includes several passageways for conductors or other components. In FIG. 9A the top portion 906 defines a passageway 914 for one or more conductors 916 that connect between a bottom portion 918 of the MEMS sensor 902 and a feed-through 920. In this example, the bottom portion 918 may include one or more electrodes or other suitable structure for connecting to the conductor(s) 916. In a similar manner as discussed above, the feed-though 920 may provide a sealing and insulating structure that enables the conductor(s) 916 to pass outside the sensor assembly 900 to be routed, for example, through an implantable lead (not shown in FIG. 9) to another device. The bottom portion 904 also defines one or more passageways 922 that enable one or more conductors or other components (not shown) to pass through the sensor assembly 900.

As mentioned above, the MEMS sensor 902 is in the form of a multilayer structure. FIGS. 9 and 10 illustrate an example of a relative orientation of these layers with respect to the housing for the sensor assembly 900. Referring to FIG. 10, three layers 1004, 1006, and 1008 are positioned in the inner space defined by the inner surfaces of the cover 908 and the bottom wall 910. The bottom portion 918 of the MEMS sensor 902 extends through an opening in the wall 910 and into the passageway 914. These and other aspects of a multilayered MEMS sensor will be discussed in more detail in conjunction with FIG. 11.

FIG. 11 illustrates several views of a MEMS sensor 1100. FIGS. 11A and 11B depict perspective and top views, respectively. FIG. 11C is a cross-section of the MEMS sensor 1100 from the perspective of view A-A of FIG. 11B. FIG. 11D is a cross-section of the MEMS sensor 1100 from the perspective of view B-B of FIG. 11C.

In some embodiments the different components of the MEMS sensor 1100 may be implemented on different layers (or levels) of the MEMS sensor 1100. For example, a primary pressure sensor 1102, a temperature sensor 1104, a reference pressure sensor 1106, and an ASIC 1108 may be implemented on different levels of the MEMS sensor 1100. FIG. 11 also illustrates an example of an internal chamber 1110 having a fixed reference pressure that may be provided adjacent the diaphragm (not shown) on a top surface of the reference pressure sensor 1106. It should be appreciated that each of the components 1102, 1104, 1106, and 1108 may be implemented as a multilayer structure. FIG. 11 also illustrates several other layers that may be attached to the MEMS sensor 1100.

A reinforcing material 1112 may be attached to a portion of the bottom of the reference pressure sensor 1106 to enhance the structural integrity (e.g., bending strength) of the MEMS sensor 1100. The reinforcing material 1112 in combination with the housing may support the MEMS sensor 1100 to withstand pressure caused by any compressive force (either static or dynamic), to protect the MEMS sensor 100 from any other loading (except the external blood pressure), and to otherwise maintain the structural integrity of the MEMS sensor 1100.

When the MEMS sensor 1100 is assembled into the sensor assembly, the reinforcing material 1112 may be configured to adjoin, but not be rigidly fixed (e.g., attached) to, the housing. In this way, the reinforcing material 1112 provide structural stability for the MEMS sensor 1100 without adversely affecting any thermal expansion or contraction of the MEMS sensor 1100.

The reinforcing material 1112 may take many forms and may be attached to the MEMS sensor 1100 in a variety of ways. In some embodiments the reinforcing material 1112 may comprise a thin sheet or membrane (e.g., on the order of 0.002 inches thick) comprising titanium, titanium alloy, or some other suitable material. The reinforcing material 1112 may be attached to the bottom surface of the silicon substrate using a bonding technique or some other suitable attachment technique. In some embodiments an insulating material may be employed between a conductive reinforcing material 1112 and the MEMS sensor 1100. In some embodiments the reinforcing material 1112 may be attached to the MEMS sensor 1100 as part of the MEMS sensor fabrication process (e.g., in a deposition process). Thus, the reinforcing material 1112 may, in effect, be integrated with the MEMS sensor 1100.

A biocompatible, and typically bio-stable, material 1114 may be attached to at least a portion of the top of the primary pressure sensor 1102. In this way, the diaphragm of the primary pressure sensor 1102 may be allowed to make direct mechanical contact with the medium (e.g., blood) from which pressure is to be measured.

The biocompatible material 1114 may take many forms. For example, the biocompatible material 1114 may be a film, a coating, or take some other suitable form. In general, any biocompatible material that may be effectively attached to a MEMS sensor and that does not unduly affect the operation of the diaphragm may be employed. In some embodiments the biocompatible material 1114 may comprise polyimide, ethylene tetrafluoroethylene ("ETFE"), diamond (e.g., a diamond-like carbon coating), carbon-based material, silicon-carbide, silicone, polyurethane, parylene, specific metal/alloy materials such as Ti6Al4V or MP35N, platinum, gold, or some combination of these or other materials.

The biocompatible material 1114 may be attached to the MEMS sensor 1100 in a variety of ways. For example, the biocompatible material 1114 may be fabricated with the MEMS sensor 1114 using chemical vapor deposition, dropping, spraying, or other suitable coating or filming techniques. In some embodiments the biocompatible material 1114 may be attached to the MEMS sensor 1110 as part of the MEMS sensor fabrication process (e.g., in a deposition process). Thus, the biocompatible material 1114 may, in effect, be integrated with the MEMS sensor 1100.

In general, the biocompatible material 1114 is adapted to be thin and deformable (e.g., flexible) so that the diaphragm of the MEMS sensor may remain flexible when subjected to external pressure loading, without significantly affecting sensor accuracy. In some embodiments the film or coating may have a thickness on the order of 0.0001-0.0005 inches. The use of a relatively thin film/coating with a relatively large ratio of diameter over thickness may also provide a negligible film/coating thermal expansion and contraction effect as compared to the pressure loading. Consequently, any deflection or deformation of the diaphragm may be predominantly caused by changes in pressure as opposed to changes in temperature or some other factor. Consequently, a MEMS sensor may achieve accurate blood pressure readings even if the temperature varies over a relatively significant range.

Through the use of MEMS technology and a thin and flexible biocompatible outer layer as taught herein, a sensor may achieve a high level of performance suitable for critical pressure measurement applications. For example, in an application where blood pressure levels are being monitored in a chamber of a patient's heart (e.g., the right ventricle), the sensor may need to be able to accurately detect relatively small changes in blood pressure. Accordingly, the sensor may have relatively high accuracy (e.g., accuracy on the order of 1 mmHg and resolution on the order of 0.5 mmHg) and stability (e.g., drift on the order of 1.0 mmHg over 3 months). Moreover, the sensor may maintain such accuracy even though it may be subjected to wide range of pressures (e.g., absolute 560 to 960 mmHg) and temperatures (e.g., 34° C. to 43° C.). In contrast some conventional techniques such as indirect mechanical pressure sensing techniques may not be able to achieve this level of performance in a practical manner due to problems associated with different temperature expansion characteristics of the sensor components and the use of relatively thin outer diaphragms (e.g., 0.0005 to 0.001 inches in width).

The biocompatible coating/film may be implemented in multiple layers to improve bonding strength and/or tearing strength. For example, referring to FIG. 12, a carbon-based material (e.g., a diamond-like carbon material) or some other suitable material 1202 that bonds effectively with silicon may be applied to (e.g., coated on) a top surface of a MEMS silicon layer 1204. A biocompatible material (e.g., Ti6Al4V, etc.) 1206 may then be applied to (e.g., coated on) a top surface of the carbon-based material 1202.

Materials, components, and manufacturing techniques similar to those described in conjunction with FIGS. 11 and 12 may be employed in a MEMS sensor that is implemented as a relatively flat component. This form of MEMS structure is depicted in FIGS. 13 and 14.

Figure 13:
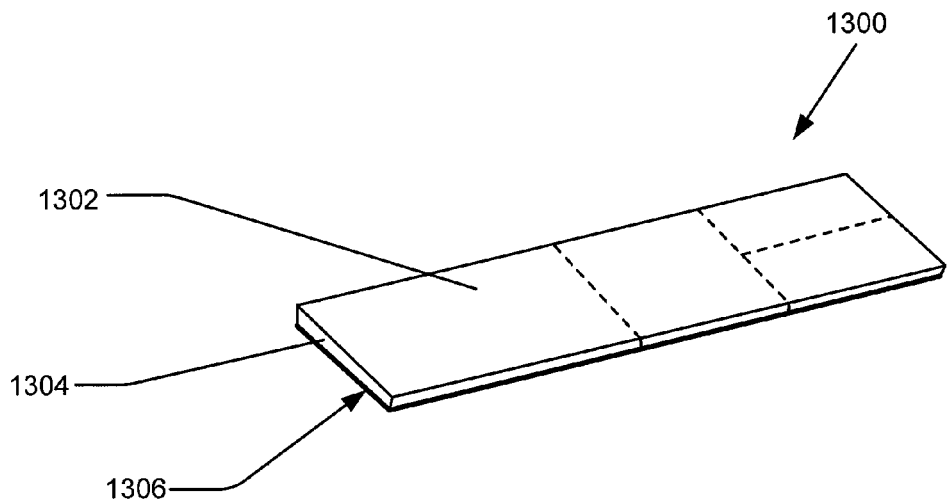
FIG. 13 is a simplified diagram of an embodiment of a MEMS sensor.
Figure 14:
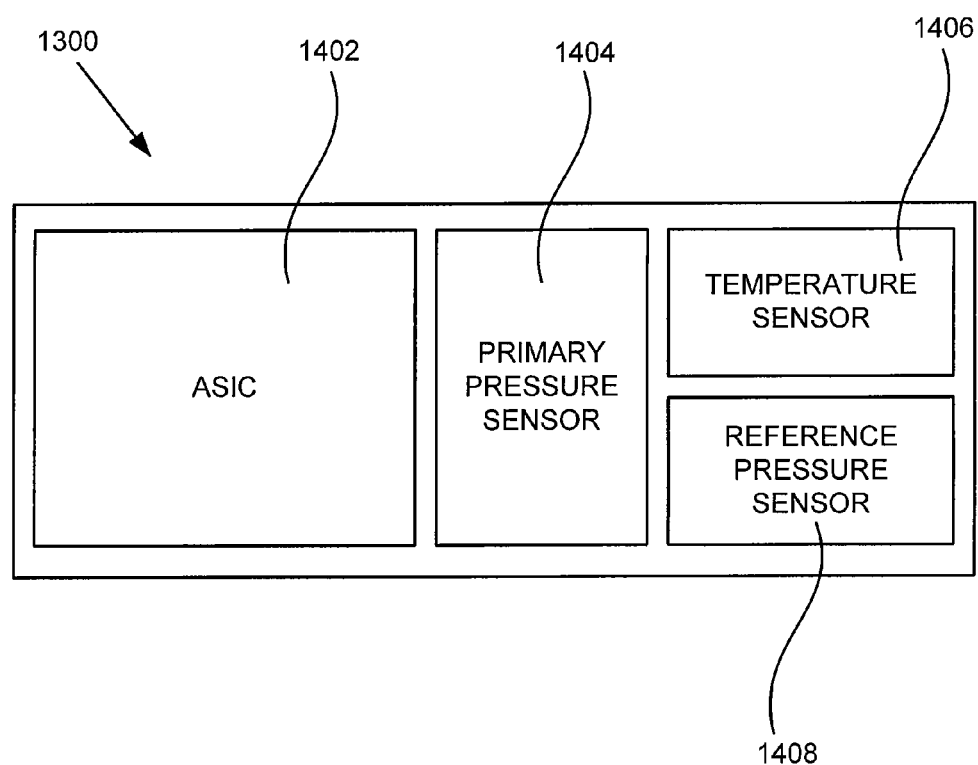
FIG. 14 is a simplified diagram of an embodiment of a MEMS sensor.

FIG. 13 illustrates an embodiment of a MEMS sensor 1300 that includes a biocompatible layer (e.g., film or coating) 1302, a MEMS substrate 1304 comprising the sensor components, and a reinforcing material (e.g., a metal sheet) 1306. In a similar manner as discussed above, the biocompatible layer 1302 is attached to at least a portion of the top surface of the MEMS substrate 1304 while the reinforcing material 1306 is attached to the bottom surface of the MEMS substrate 1304.

In some embodiments the MEMS sensor 1300 is dividing into several regions to implement the functionality of the sensors and other components of the MEMS sensor 1300. For example, referring to FIG. 14 a first region 1402 may include at least a portion of the functionality of the ASIC described herein. A second region 1404 may include at least a portion of the functionality of the primary pressure sensor. A third region 1406 may include at least a portion of the functionality of the temperature sensor. A fourth region 1408 may include at least a portion of the functionality of the reference pressure sensor.

In the embodiments of FIGS. 11-13 the biocompatible material was depicted as being attached to the MEMS sensor. In practice, the biocompatible material may be attached to other components of a MEMS sensor assembly. FIG. 15 illustrates several different examples of how a biocompatible material may be incorporated into a MEMS assembly 1500.

Figure 15A:
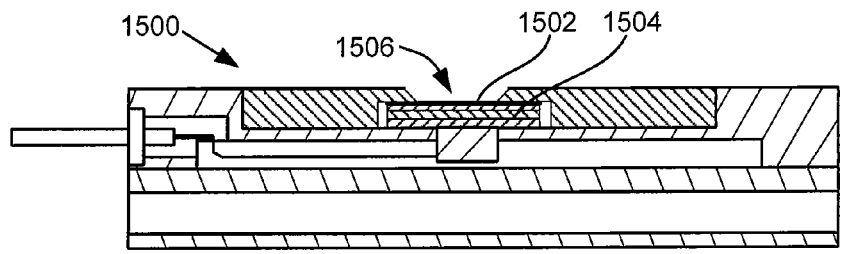
FIGS. 15A, 15B, 15C, and 15D, illustrates various simplified cross-sectional views of an embodiment of a sensor assembly.

FIG. 15A illustrates an embodiment where a biocompatible material 1502 is attached to at least a portion of a top surface of a MEMS sensor 1504. In this case, the attaching process may be performed before the MEMS sensor 1504 is assembled into the sensor assembly 1500. The biocompatible material 1502 protects the diaphragm (not shown) of the MEMS sensor 1504 from blood or any other bodily fluid or tissue that would otherwise enter the window 1506 and thereby come in contact with the outer surface of the diaphragm. In the embodiment of FIG. 15A, appropriate provisions also may be made to ensure that an adequate seal is provided between the top of the biocompatible material 1502 and the portion of the housing that contacts the top of the biocompatible material 1502.

Figure 15B:
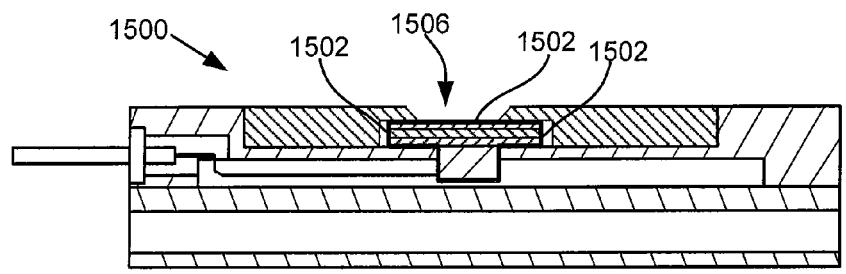

FIG. 15B illustrates an embodiment where a biocompatible material 1502 is attached around an entire outer surface of a MEMS sensor. In this case, the attaching process is performed before the MEMS sensor is assembled into the sensor assembly 1500. Again, the biocompatible material 1502 protects the diaphragm (not shown) of the MEMS sensor. In addition, appropriate provisions also may be made to ensure that an adequate seal is provided between the biocompatible material 1502 and at least a portion of the housing that contacts the biocompatible material. In a typical embodiment, this seal would be implemented in areas around the opening 1506.

Figure 15C:
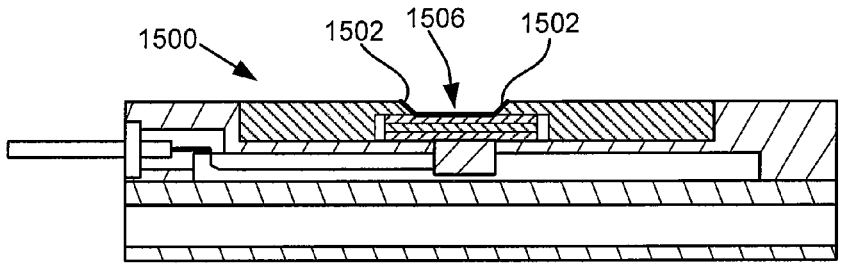

FIG. 15C illustrates an embodiment where a biocompatible material 1502 is attached to a portion of an outer surface of a MEMS sensor and to the sidewalls defining the window 1506. In this case, the attaching process may be performed after the MEMS sensor is assembled into the sensor assembly 1500. In this way, the biocompatible material may serve to provide an adequate seal between the housing and the MEMS sensor in the area around the opening 1506.

Figure 15D:
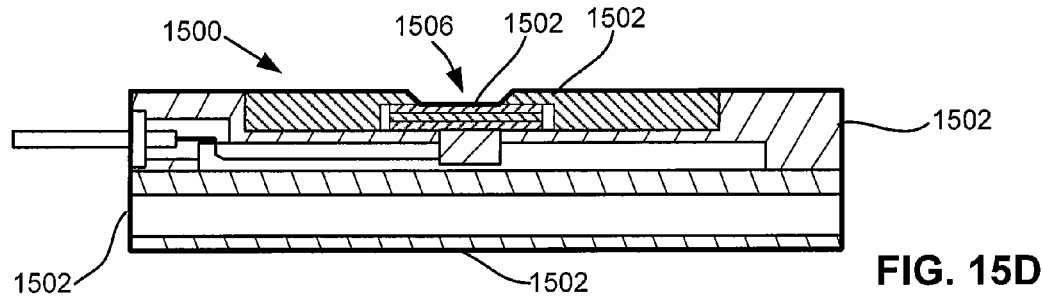

FIG. 15D illustrates an embodiment where the biocompatible material 1502 extends around and is attached to the entire outer surface of the MEMS structure 1500, including a portion of an outer surface of a MEMS sensor and the sidewalls defining the window 1506. In this case, the attaching process may be performed after the MEMS sensor is assembled into the sensor assembly 1500 whereby the biocompatible material serves to provide an adequate seal between the housing and the MEMS sensor in the area around the opening 1506. It should be appreciated that the implementation of FIG. 15D may be used in conjunction with a non-biocompatible housing material.

A sensor as taught herein may be incorporated into or used with various types of components to achieve the desired pressure sensing. In a typical implementation a sensor may be incorporated into an implantable lead. Through the use of the teachings herein the sensor, and hence the sensor assembly, may advantageously be constructed of a sufficiently small size and weight to facilitate incorporation of the sensor assembly into the implantable lead. For example, in some embodiments a sensor assembly incorporating a MEMS sensor may have an outside diameter on the order of 2-9 French and a length on the order of 0.10 to 0.40 inches. Consequently, the sensor assembly may be effectively incorporated into a lead (e.g., sensing lead, pacing lead, defibrillation lead, or catheter) having a diameter on the order of 2-9 French. Moreover, given that a smaller housing size may result in a lower overall weight for the sensor assembly, lead stability over time may be improved as compared to conventional sensors, due to lower dynamic motion impact on the lead. In a specific example that may advantageously be used with a lead having an outside diameter on the order of 4 French, the sensor assembly may have an outside diameter on the order of 4 French and a length on the order of 0.25 inches.

A MEMS sensor assembly may be incorporated into a lead in various ways. For example, a MEMS sensor assembly may be incorporated between opposing lead body sections or on an end of a lead body. The MEMS sensor assembly (e.g., exterior portions of the sensor housing) may be attached to the lead body (e.g., constructed of silicone, polyurethane, or some other suitable material) using various mechanisms including, for example, adhesives or welding. In some implementations the MEMS sensor assembly may be substantially co-circumferential with the body of the lead.

A MEMS sensor assembly may be incorporated into various types of leads. In some embodiments a MEMS sensor may be incorporated into a dedicated lead. In such a case, the passageway in the bottom portion of the sensor assembly (e.g. passageway 726) may not be implemented.

In some embodiments a MEMS sensor may be incorporated into a cardiac lead. Such a lead may include other components for sensing conditions in and providing therapy to a patient. An example embodiment of a cardiac lead will be discussed in some detail in conjunction with FIG. 16.

Figure 16:
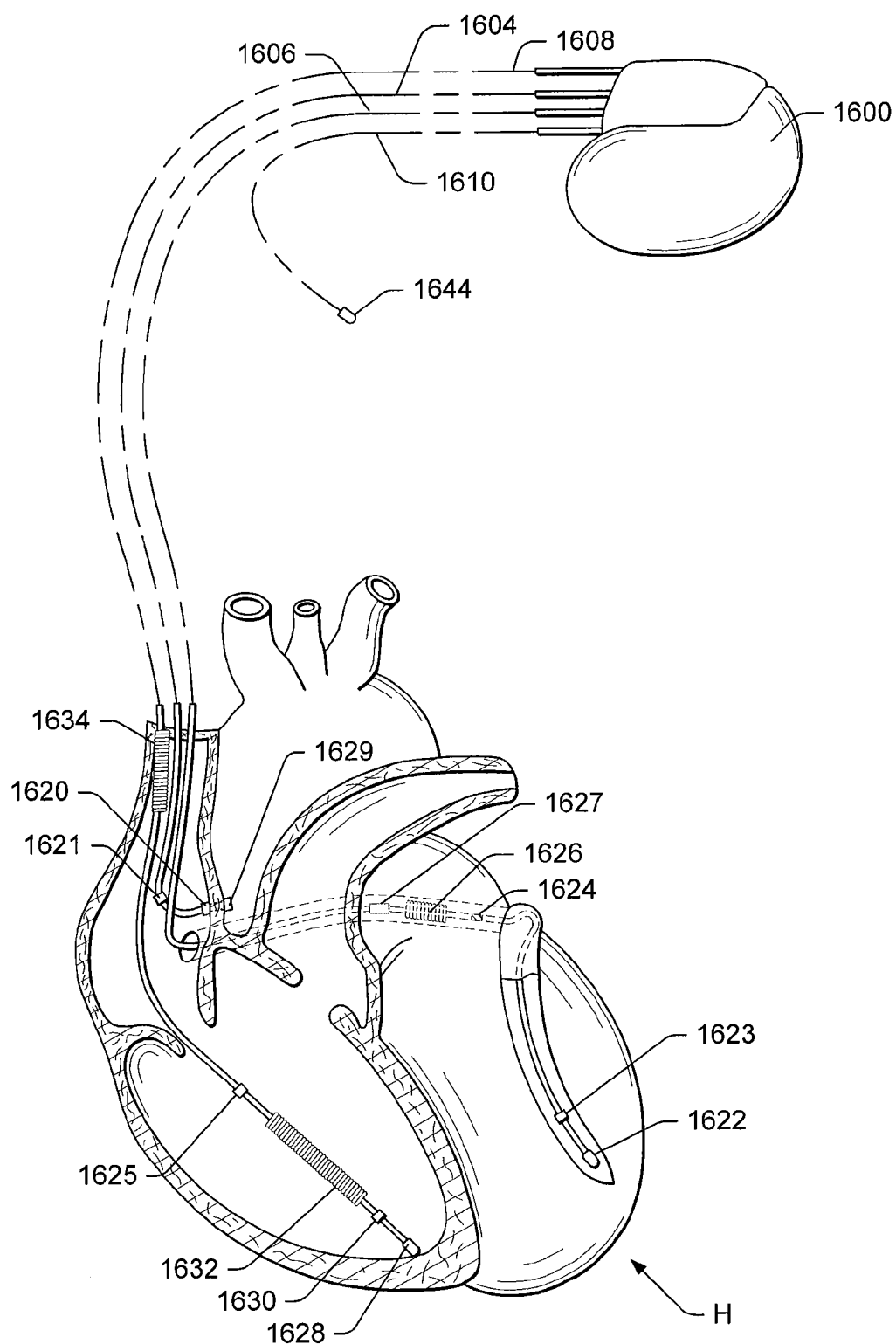
FIG. 16 is a simplified diagram of an embodiment of an implantable stimulation device in electrical communication with one or more leads implanted in a patient's heart for sensing conditions in the patient, delivering therapy to the patient, or providing some combination thereof.

In FIG. 16 pressure monitoring may be performed in conjunction with an implantable cardiac device (e.g., a stimulation device such as an implantable cardioverter defibrillator, a pacemaker, etc.). Here, one or more of the operations described above may be implemented in or in conjunction with such an implantable cardiac device. It should be appreciated that this example is provided for explanatory purposes and that pressure monitoring may be implemented using other types of devices. It also should be appreciated and understood that other cardiac devices, including those that are not necessarily implantable, may be used in conjunction with the teachings herein.

FIG. 16 illustrates an implantable cardiac device 1600 in electrical communication with a patient's heart H by way of three leads 1604, 1606, and 1608, suitable for delivering multi-chamber stimulation and shock therapy. To sense atrial cardiac signals and to provide right atrial chamber stimulation therapy, the device 1600 is coupled to an implantable right atrial lead 1604 having, for example, an atrial tip electrode 1620, which typically is implanted in the patient's right atrial appendage or septum. FIG. 16 also shows the right atrial lead 1604 as having an optional atrial ring electrode 1621.

To sense left atrial and ventricular cardiac signals and to provide left chamber pacing therapy, device 1600 is coupled to a coronary sinus lead 1606 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 1606 is designed to receive atrial and ventricular cardiac signals and to deliver left ventricular pacing therapy using, for example, a left ventricular tip electrode 1622 and, optionally, a left ventricular ring electrode 1623; provide left atrial pacing therapy using, for example, a left atrial ring electrode 1624; and provide shocking therapy using, for example, a left atrial coil electrode 1626 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 1600 is also shown in electrical communication with the patient's heart H by way of an implantable right ventricular lead 1608 having, in this implementation, a right ventricular tip electrode 1628, a right ventricular ring electrode 1630, a right ventricular (RV) coil electrode 1632 (or other electrode capable of delivering a shock), and a superior vena cava (SVC) coil electrode 1634 (or other electrode capable of delivering a shock). Typically, the right ventricular lead 1608 is transvenously inserted into the heart H to place the right ventricular tip electrode 1628 in the right ventricular apex so that the RV coil electrode 1632 will be positioned in the right ventricle and the SVC coil electrode 1634 will be positioned in the superior vena cava. Accordingly, the right ventricular lead 1608 is capable of sensing or receiving cardiac signals, and delivering stimulation in the form of pacing and shock therapy to the right ventricle.

Any of the leads 1604, 1606, and 1608 may include one or more pressure sensors as taught herein for measuring pressure in a chamber or vessel of the heart H. Here, pressure signals generated by a pressure sensor are transmitted to the device 1600 via one or more conductors that run through a corresponding cardiac lead. The device 1600 may then utilize the corresponding pressure readings to commence or alter therapy for the patient, or to forward the pressure information to a device that is external to the patient.

In a typical embodiment, a pressure sensor 1625 (e.g., a MEMS sensor assembly as taught herein) incorporated with the body of the lead 1608 may measure pressure in the right ventricle. In this case, conductors associated with other components of the lead 1608 (e.g., electrodes 1628, 1630, and 1632) may be routed through the passageway(s) in the bottom portion of the sensor assembly (e.g. passageway 726).

In some embodiments the right atrial lead 1604 or some other lead may be implanted in the septal wall (e.g., in the area of the fossa ovalis) separating the right atrium and the left atrium to measure pressure in the left atrium. For example, the lead 1604 may include a pressure sensor 1629 (e.g., a MEMS sensor assembly as taught herein) located on a distal portion of the lead. Alternatively, the pressure sensor 1629 may be located at some other location along the lead and coupled to receive pressure waves from the left atrium.

In some embodiments, a pressure sensor 1627 on the lead 1606 may be adapted to measure pressure in the heart. It should be appreciated that pressure may be measured in various chambers or vessels of the body and that other mechanisms may be employed to measure pressure in a given chamber or vessel.

The device 1600 is also shown in electrical communication with a lead 1610 including one or more components 1644 such as a physiologic sensor. The component 1644 may be positioned in, near or remote from the heart.

The device 1600 may connect to leads other than those specifically shown. In addition, the leads connected to the device 1600 may include components other than those specifically shown. For example, a lead may include other types of electrodes, sensors or devices that serve to otherwise interact with a patient or the surroundings.

It should be appreciated that various modifications may be employed in conjunction with the disclosed embodiments based on the teachings herein. For example, different techniques may be employed to protect the MEMS sensor from blood, other bodily fluid, or tissue. In addition, various MEMS-based technologies may be employed to implement a MEMS sensor. Also, various algorithms or techniques may be employed to obtain pressure readings and to calibrate or otherwise adjust the readings.

Various techniques may be employed to support a MEMS sensor in a MEMS sensor assembly. For example, different spacings between the MEMS sensor assembly and the housing may be employed in different applications depending on the range of temperature fluctuations and the amount of stress, etc., that are expected for the applications. In addition, different techniques may be employed to compensate for expansion or contraction of the MEMS sensor.

The structure and functionality taught herein may be incorporated into types of devices other than those types specifically described. For example, a MEMS sensor may be incorporated into other types of implantable leads or may be implanted or otherwise provided without the use of leads. These sensors may be located at various positions throughout the heart or the body.

It should be appreciated from the above that the various structures and functions described herein may be incorporated into a variety of apparatuses (e.g., a lead, a monitoring device, a stimulation device, etc.) and implemented in a variety of ways. Different embodiments of the stimulation device may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components by the code or to execute the code) may be stored in an appropriate data memory that is readable by a processing device (e.g., commonly referred to as a computer-readable medium).

Moreover, some of the operations described herein may be performed by a device that is located externally with respect to the body of the patient. For example, an implanted device may simply send raw data or processed data to an external device that then performs the necessary processing.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, implemented as discrete wires, or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, etc. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

While certain exemplary embodiments have been described above in detail and shown in the accompanying drawings, it is to be understood that such embodiments are merely illustrative of and not restrictive of the broad invention. In particular, it should be recognized that the teachings herein apply to a wide variety of apparatuses and methods. It will thus be recognized that various modifications may be made to the illustrated and other embodiments described above, without departing from the broad inventive scope thereof. In view of the above it will be understood that the invention is not limited to the particular embodiments or arrangements disclosed, but is rather intended to cover any changes, adaptations or modifications which are within the scope of the invention as defined by the appended claims.

What is claimed is:

1. An implantable lead, comprising:
    a lead body;
    a sensor housing attached to the lead body; and
    a micro-electromechanical system (MEMS) sensor enclosed within the sensor housing and comprising:
        a primary pressure sensor generating primary pressure signals indicative of a primary pressure measured by the primary pressure sensor;
        a reference pressure sensor generating reference pressure signals indicative of a secondary pressure measured by the secondary pressure sensor; and
        a compensation circuit generating a compensated pressure reading based on the primary pressure signals and the reference pressure signals.

2. The implantable lead of claim 1, comprising a temperature sensor generating temperature signals indicative of a temperature measured by the temperature sensor, wherein the pressure compensation circuit is adapted to adjust the primary pressure signals based on the temperature signals.

3. The implantable lead of claim 1, wherein the sensor housing comprises a sealed chamber, the sealed chamber maintaining a known pressure for the reference pressure sensor.

4. The implantable lead of claim 1, wherein the MEMS sensor comprises:
    a first layer comprising the primary pressure sensor;
    a second layer comprising the temperature sensor; and
    a third layer comprising the reference pressure sensor.

5. A method of measuring pressure in a heart of a patient, comprising:
    generating a primary pressure reading from a primary pressure sensor of an implanted micro-electromechanical system (MEMS) sensor;
    generating a reference pressure reading from a reference pressure sensor of the MEMS sensor; and
    generating a temperature compensated pressure reading based on the primary pressure reading and the reference pressure reading.

6. The method of claim 5, further comprising generating a temperature reading from a temperature sensor of the MEMS sensor, wherein the generation of the temperature compensated pressure reading is further based on the temperature reading.

* * * * *